(12) United States Patent
Chowienczyk et al.

(10) Patent No.: US 6,908,436 B2
(45) Date of Patent: Jun. 21, 2005

(54) METHOD OF MEASURING ENDOTHELIAL FUNCTION IN A PERSON

(75) Inventors: Philip Jan Chowienczyk, London (GB); Christopher Patrick Lawson, Rochester (GB); Sandrine Celine Millasseau, Morden (GB)

(73) Assignee: Micro Medical Ltd, Rochester (GB)

( * ) Notice: Subject to any disclaimer, the term of this patent is extended or adjusted under 35 U.S.C. 154(b) by 0 days.

(21) Appl. No.: 10/385,580

(22) Filed: Mar. 11, 2003

(65) Prior Publication Data

US 2003/0229288 A1 Dec. 11, 2003

(51) Int. Cl.[7] ................................................. A61B 5/00
(52) U.S. Cl. ...................................... 600/500; 600/485
(58) Field of Search ......................... 600/485, 500–503, 600/490, 504

(56) References Cited

U.S. PATENT DOCUMENTS

| 6,152,881 | A | * | 11/2000 | Raines et al. ............... 600/507 |
| 6,322,515 | B1 | * | 11/2001 | Goor et al. .................. 600/485 |
| 6,338,719 | B1 | * | 1/2002 | Drzewiecki et al. ........ 600/490 |
| 6,654,628 | B1 | * | 11/2003 | Silber et al. ................. 600/410 |
| 6,719,704 | B2 | * | 4/2004 | Narimatsu et al. .......... 600/500 |

FOREIGN PATENT DOCUMENTS

| WO | WO 01 95798 A2 | 12/2001 |
| WO | WO 01 95798 A3 | 12/2001 |
| WO | WO 02 00107 A3 | 1/2002 |
| WO | WO 02 00107 A2 | 1/2002 |
| WO | WO 02 34105 A2 | 5/2002 |

OTHER PUBLICATIONS

Anderson, Todd J, "Assessment and Treatment of Endothelial Dysfunction in Humans" JACC, vol. 34, No. 3, 1999, pp. 631–638.

* cited by examiner

*Primary Examiner*—Robert L. Nasser
(74) *Attorney, Agent, or Firm*—Iandiorio & Teska

(57) ABSTRACT

A method of measuring endothelial function in a person (2), which method comprises applying pressure to one arm of the person (2) such as to restrict blood flow in the arm (6), releasing the pressure in order to cause an increase in blood flow in the arm (6) due to reactive hyperaemia, and then measuring the difference in pulse propagation time between the two arms (6, 8) of the person.

7 Claims, 1 Drawing Sheet

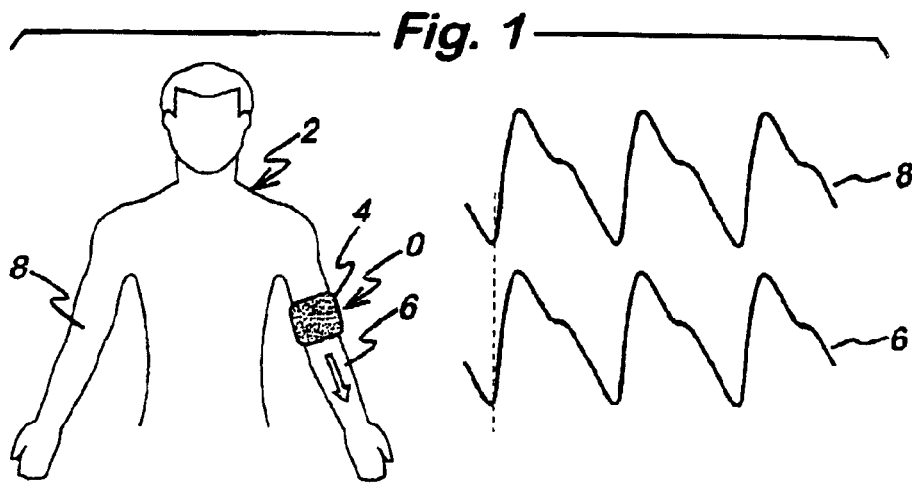
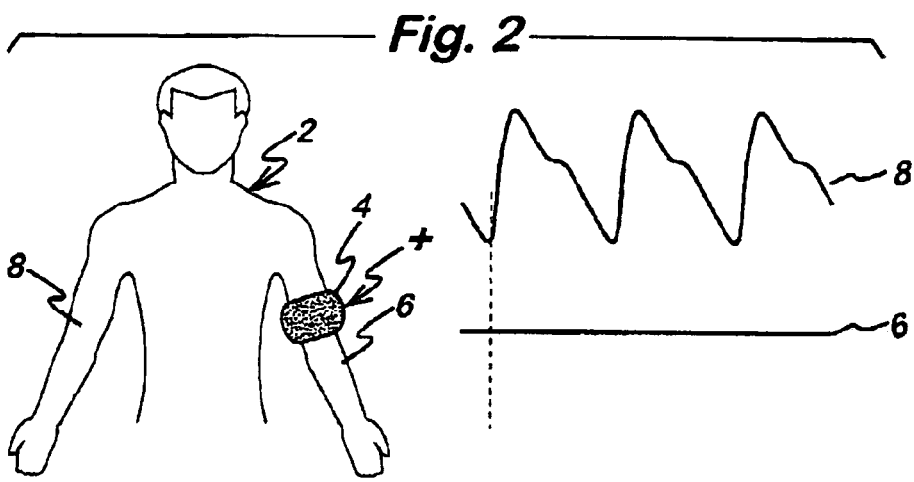
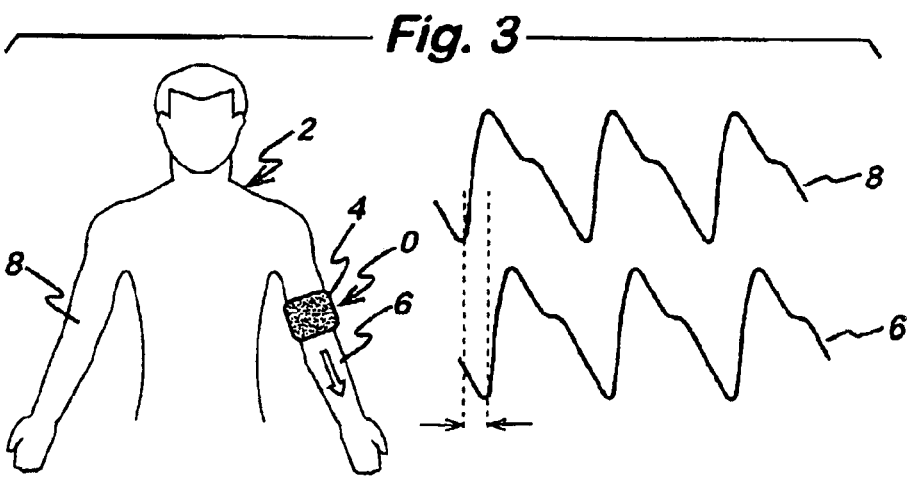

METHOD OF MEASURING ENDOTHELIAL FUNCTION IN A PERSON

This invention relates to a method of measuring endothelial function in a person.

A major cause of death in the developed world is atherosclerotic arterial disease. The atherosclerotic arterial disease is thought to be initiated by injury to the endothelium. There has thus been intense interest in the observation that the endothelium-dependent vasomotor function mediated by nitric oxide is abnormal early in the development of vascular disease, and indeed in the pre-clinical phase of the arterial disease when risk factors alone are present. In addition to inhibitory actions on platelets and on the proliferation of vascular smooth muscle, nitric oxide inhibits the expression of adhesion molecules, a key event in the process of endothelial activation and atherogenesis. Impaired bioactivity of nitric oxide is thus likely to explain the link between endothelial vasomotor dysfunction and the development of athorosclerosis.

Current techniques for the evaluation of endothelial function in vivo are based on determining the vasomotor response to pharmacological or physical stimuli. Pharmacological techniques usually involve intra-arterial injection of an endothelium-dependent vasodilator, usually acetylcholine. The requirement of arterial canulation precludes their use outside specialised vascular laboratories. The technique now more frequently employed is that in which the vasomotor response of the brachial artery to an increase in blood flow is assessed by ultrasonography. Reactive hyperaemia in a person's distal forearm is used to generate an increase in blood flow in the brachial artery. The reactive hyperaemia may be achieved by a 4–5 inflation of a cuff applied around the forearm to a suprasystolic pressure. The resulting increase in blood flow produces a flow mediated dilation of the brachial artery in the order 5–10%. This change in diameter can be determined using high resolution duplex ultrasound imaging. The change in diameter is largely nitric oxide-dependent, and it is attenuated in persons with endothelial dysfunction. The magnitude of the change is, however, close to the limits of resolution of current imaging techniques and this limits the reproducibility of the method. A number of refinements based upon automatic edge detection have been introduced to improve this but with limited success. A further drawback of the technique is that it is to some extent dependent on the exact position within the artery at which measurements are made.

Acceptable results can only be obtained with great attention to detail. A skilled operator is essential in order to ensure correct transducer placement. The transducer must then be held throughout the course of the measurement, during which time the subject must remain motionless. These practical constraints mean that, although the method is non-invasive, it effectively shares the drawback of intra-arterial methods in that it is only applicable within a specialist laboratory.

It is an aim of the present invention to provide a method of measuring endothelial function in a person, which method obviates or reduces the above mentioned problems with the currently used techniques.

Accordingly, in one non-limiting embodiment of the present invention there is provided a method of measuring endothelial function in a person, which method comprises applying pressure to one arm of the person such as to restrict blood flow in the arm, releasing the pressure in order to cause an increase in blood flow in the arm due to reactive hyperaemia, and then measuring the difference in pulse propagation time between the two arms of the person.

The method may be one in which the pressure is applied to the arm using restrictor means. The restrictor means is preferably an inflatable restrictor means but other types of restrictor means may be employed. A presently preferred inflatable restrictor means is a blood pressure cuff.

The method of the present invention is preferably one in which the difference in pulse propagation time is measured using photoplethysmography. Other techniques may be used for measuring the pulse propagation time if desired. Preferably, the photoplethysmography comprises measuring the transmission/absorption of infra red light through/in the finger pulp of the person.

The method of the present invention may be such that it uses the same stimulus of post-occlusive hyperaemia to release nitric oxide as in the above mentioned known assessment of flow mediated dilation. Post occlusive hyperaemia in the arm results not only in an increase in diameter of the arteries in the arm, but also in an increase in the distensibility of these arteries. This, in turn, results in a decrease in pulse wave velocity and delays the arrival of the pulse in the radial and digital arteries relative to that in central arteries and in the contralateral arm. Measurements of the time of arrival of the pulse in both hands or arms simultaneously allows the delay in arrival of the pulse to be determined accurately in relation to the contralateral arm. Use of the contralateral arm in this way serves to control for factors, for example a change in blood pressure, which affect both arms equally. In addition to its simplicity, a further advantage of the method of the present invention is that the change in pulse wave velocity represents an integrated measure of flow induced change in all conduit arteries of the upper limb, rather than at a single point as is the case with flow mediated dilation. The method of the present invention may be such that it is reproducible and sensitive in detecting endothelial dysfunction.

As mentioned above, one method for measuring the time of arrival of the pulse is to obtain a digital volume pulse by measuring the transmission/absorption of infra red light through/in the finger pulp. The timing of the pulse so obtained bears a constant relationship to that of the radial pulse.

An embodiment of the invention will now be described solely by way of example and with reference to the accompanying drawings in which:

FIG. 1 illustrates a first step in a method of measuring endothelial function in a person;

FIG. 2 illustrates a second step in the method of measuring the endothelial function in the person; and FIG. 3 illustrates a third step in the method of measuring the endothelial function in the person.

Referring to the drawings, there is shown a person 2 having their endothelial function being measured. The method of measuring the endothelial function in the person 2 comprises applying pressure with a restrictor means 4 to one arm 6 of the person 2 such as to restrict blood flow in the arm. The restrictor means 4 is an inflatable restrictor means in the form of a blood pressure cuff as shown. After the pressure has been applied, subsequent releasing of the pressure causes an increase in blood flow in the arm 6 due to reactive hyperaemia. The endothelial function is then obtained by measuring the difference in pulse propagation time between the two arms 6, 8 of the person 2.

FIG. 1 indicates by the arrow "O" that the restrictor means 4 is deflated. As also shown in FIG. 1, the pulses obtained from the right arm 6 and the left arm 8 coincide.

FIG. 2 indicates by the arrow "+" that the restrictor means 4 has been inflated to a pressure above systolic blood pressure. The pulse from the left arm 6 is occluded as shown in FIG. 8.

FIG. 3 shows by the arrow "O" that the restrictor means 4 on the left arm 6 has been deflated. This causes an increase in blood flow in the left arm 6 due to the reactive hyperaemia. This in turns leads to endothelium-dependent dilation of the arteries in the left arm 6. This in turn results in a delay in the pulse in the left arm 6 relative to the pulse in the right arm 8. This delay is a measure of the endothelial function. The delay time is proportional to the function of the endothelium in causing dilation of the artery following reactive hyperaemia. The delay time can therefore be used as a direct measure of endothelial function. Poor endothelial function is associated with little or no delay time, whereas good endothelial function is associated with a delay time of 10 milliseconds or greater. The measured endothelial function is then able to give an indication of whether or not the person 2 is at risk of suffering from atherosclerotic arterial disease.

It is to be appreciated that the embodiment of the invention described above with reference to the accompanying drawings has been given by way of example only and that modifications may be effected. Thus, for example, restrictor means 4 other than the illustrated blood pressure cuff could be employed. An alternative means to register the pulses in the two arms may be used. Such an alternative means could be the use of flow or pressure transducers placed over arteries in the wrist or hand.

What is claimed is:

1. A method of measuring endothelial function in a person, which method comprises applying pressure to one arm of the person such as to restrict blood flow in the arm, releasing the pressure in order to cause an increase in blood flow in the arm due to reactive hyperaemia, and then measuring the difference in pulse propagation time between the two arms of the person.

2. A method according to claim 1 in which the pressure is applied to the arm using restrictor means.

3. A method according to claim 2 in which the restrictor means is an inflatable restrictor means.

4. A method according to claim 3 in which the inflatable restrictor means is a blood pressure cuff.

5. A method according to claim 1 in which the difference in pulse propagation time is measured using photoplethysmography.

6. A method according to claim 5 in which the photoplethysmography comprises measuring the transmission/absorption of infra red light through/in the finger pulp of the person.

7. A method according to claim 1 in which the difference in the pulse propagation time between the two arms of the person is taken as a direct and continuous measure of the endothelial function.

* * * * *